United States Patent
Lloyd

Patent Number: 5,308,762
Date of Patent: May 3, 1994

[54] T4 ENDONUCLEASE V DNA REPAIR ENZYME HAVING SPECIFIC ACTIVITY AT LOW SALT CONCENTRATIONS

[75] Inventor: R. Stephen Lloyd, Nashville, Tenn.

[73] Assignee: Vanderbilt University, Nashville, Tenn.

[21] Appl. No.: 827,506

[22] Filed: Jan. 27, 1992

Related U.S. Application Data

[63] Continuation-in-part of Ser. No. 401,916, Sep. 1, 1989, abandoned.

[51] Int. Cl.$^5$ ............................................. C12N 9/22
[52] U.S. Cl. .................................. 435/199; 435/172.3; 935/10; 935/14
[58] Field of Search .................................. 536/23.2

[56] References Cited

PUBLICATIONS

Recinos et al. (1986) J. Bacteriol. 168:1014–1018.
Recinos et al (1988) Biochem. 27:1832–1838.
Lloyd et al (1989) Proteins Struc. Funct. Genet. 6:128–138.
Recinos, A., et al. "Expression of the bacteriophage T4 denV structural gene in Escherichia coli" 1986. J. Bacteriol. 168:1014–1018.
Recinos, A. & Lloyd, R. S. "Site directed mutagenesis of the T4 Endonuclease V Gene: Role of Lysine-130" 1988 Biochemistry 27:1832–1838.
Lloyd, R. S. & Augustine, M. L. "Site directed mutagenesis of the T4 Endonuclease V Gene: Mutations which Enhance Enzyme Specific Activity at Low Salt Concentrations" 1989 Proteins Struct. Funct. Genet. 6:128–138.

*Primary Examiner*—Robert A. Wax
*Assistant Examiner*—Gabriele E. Bugalsky
*Attorney, Agent, or Firm*—Reising, Ethington, Barnard, Perry & Milton

[57] ABSTRACT

A T4 endonuclease V DNA repair enzyme contains an amino acid sequence within its carboxyl terminal region which is involved in dimer specific binding. The region includes polar nonaromatic basic amino acids and aromatic amino acids between amino acid 128 to 137 positions. The specific activity of the enzyme is greatly increased at low salt concentrations when substitutions are made in aromatic amino acids in the carboxy terminal region.

6 Claims, 5 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( i x ) FEATURE:
        ( A ) NAME/KEY: CDS
        ( B ) LOCATION: 1..417

( i x ) FEATURE:
        ( A ) NAME/KEY: mutation
        ( B ) LOCATION: replace(386..387, "")

( i x ) FEATURE:
        ( A ) NAME/KEY: miscfeature
        ( B ) LOCATION: 385..387

( x i ) SEQUENCE DESCRIPTION: SEQ ID NO:1:

```
ATG  ACT  CGT  ATC  AAC  CTT  ACT  TTA  GTA  TCT  GAA  TTG  GCT  GAC  CAA  CAC        48
Met  Thr  Arg  Ile  Asn  Leu  Thr  Leu  Val  Ser  Glu  Leu  Ala  Asp  Gln  His
 1              5                        10                      15

TTA  ATG  GCT  GAA  TAT  CGT  GAA  TTG  CCG  CGT  GTT  TTT  GGT  GCA  GTT  CGT        96
Leu  Met  Ala  Glu  Tyr  Arg  Glu  Leu  Pro  Arg  Val  Phe  Gly  Ala  Val  Arg
              20                       25                       30

AAG  CAT  GTT  GCT  AAC  GGT  AAA  CGT  GTT  CGT  GAT  TTT  AAA  ATC  AGT  CCT       144
Lys  His  Val  Ala  Asn  Gly  Lys  Arg  Val  Arg  Asp  Phe  Lys  Ile  Ser  Pro
         35                       40                       45

ACT  TTT  ATC  CTT  GGC  GCA  GGT  CAT  GTT  ACA  TTC  TTT  TAC  GAT  AAG  CTC       192
Thr  Phe  Ile  Leu  Gly  Ala  Gly  His  Val  Thr  Phe  Phe  Tyr  Asp  Lys  Leu
         50                       55                       60
```

| | | | | | | | | | | | | | | | | |
|---|---|---|---|---|---|---|---|---|---|---|---|---|---|---|---|---|
|GAG|TTC|TTA|CGT|AAA|CGT|CAA|ATT|GAG|CTT|ATA|GCT|GAA|TGT|TTA|AAA|240|
|Glu|Phe|Leu|Arg|Lys|Arg|Gln|Ile|Glu|Leu|Ile|Ala|Glu|Cys|Leu|Lys| |
|65| | | |70| | | |75| | | | | | |80| |
|CGT|GGT|TTT|AAT|ATC|AAG|GAT|ACT|ACA|GTC|CAG|GAT|ATT|AGT|GAT|ATT|288|
|Arg|Gly|Phe|Asn|Ile|Lys|Asp|Thr|Thr|Val|Gln|Asp|Ile|Ser|Asp|Ile| |
| | | | |85| | | | |90| | | | |95| | |
|CCT|CAG|GAA|TTC|CGT|GGT|GAT|TAT|ATT|CCC|CAT|GAA|GCT|TCT|ATT|GCT|336|
|Pro|Gln|Glu|Phe|Arg|Gly|Asp|Tyr|Ile|Pro|His|Glu|Ala|Ser|Ile|Ala| |
| | | |100| | | | |105| | | | |110| | | |
|ATA|TCA|CAA|GCT|CGT|TTA|GAT|GAA|AAA|ATT|GCA|CAA|CGT|CCT|ACT|TGG|384|
|Ile|Ser|Gln|Ala|Arg|Leu|Asp|Glu|Lys|Ile|Ala|Gln|Arg|Pro|Thr|Trp| |
| | |115| | | | |120| | | | |125| | | | |
|TTT|AAA|TAC|TAC|GGT|AAG|GCG|ATT|TAT|GCA|TAA| | | | | |417|
|Phe|Lys|Tyr|Tyr|Gly|Lys|Ala|Ile|Tyr|Ala| | | | | | | |
| |130| | | | |135| | | | | | | | | | |

(2) INFORMATION FOR SEQ ID NO:2:

(i) SEQUENCE CHARACTERISTICS:
        (A) LENGTH: 138 amino acids
        (B) TYPE: amino acid
        (D) TOPOLOGY: linear     (ii) MOLECULE TYPE: protein     (xi) SEQUENCE DESCRIPTION: SEQ ID NO:2:

Met Thr Arg Ile Asn Leu Thr Leu Val Ser Glu Leu Ala Asp Gln His
1               5                   10                  15

Leu Met Ala Glu Tyr Arg Glu Leu Pro Arg Val Phe Gly Ala Val Arg
            20                  25                  30

Lys His Val Ala Asn Gly Lys Arg Val Arg Asp Phe Lys Ile Ser Pro
        35                  40                  45

Thr Phe Ile Leu Gly Ala Gly His Val Thr Phe Phe Tyr Asp Lys Leu
    50                  55                  60

Glu Phe Leu Arg Lys Arg Gln Ile Glu Leu Ile Ala Glu Cys Leu Lys
65                  70                  75                  80

Arg Gly Phe Asn Ile Lys Asp Thr Thr Val Gln Asp Ile Ser Asp Ile
                85                  90                  95

Pro Gln Glu Phe Arg Gly Asp Tyr Ile Pro His Glu Ala Ser Ile Ala
            100                 105                 110

Ile Ser Gln Ala Arg Leu Asp Glu Lys Ile Ala Gln Arg Pro Thr Trp
        115                 120                 125

Phe Lys Tyr Tyr Gly Lys Ala Ile Tyr Ala
    130                 135

(2) INFORMATION FOR SEQ ID NO:3:

(i) SEQUENCE CHARACTERISTICS:
        (A) LENGTH: 417 base pairs
        (B) TYPE: nucleic acid
        (C) STRANDEDNESS: single
        (D) TOPOLOGY: linear     (ii) MOLECULE TYPE: DNA (genomic)

(ix) FEATURE:
        (A) NAME/KEY: CDS
        (B) LOCATION: 1..417

(ix) FEATURE:
        (A) NAME/KEY: mutation
        (B) LOCATION: replace(386..387, "")

(ix) FEATURE:
        (A) NAME/KEY: miscfeature
        (B) LOCATION: 385..387

(x i) SEQUENCE DESCRIPTION: SEQ ID NO:3:

| | | | | | | | | | | | | | | | | |
|---|---|---|---|---|---|---|---|---|---|---|---|---|---|---|---|---|
| ATG | ACT | CGT | ATC | AAC | CTT | ACT | TTA | GTA | TCT | GAA | TTG | GCT | GAC | CAA | CAC | 48 |
| Met | Thr | Arg | Ile | Asn | Leu | Thr | Leu | Val | Ser | Glu | Leu | Ala | Asp | Gln | His | |
| 1 | | | | 5 | | | | | 10 | | | | | 15 | | |
| TTA | ATG | GCT | GAA | TAT | CGT | GAA | TTG | CCG | CGT | GTT | TTT | GGT | GCA | GTT | CGT | 96 |
| Leu | Met | Ala | Glu | Tyr | Arg | Glu | Leu | Pro | Arg | Val | Phe | Gly | Ala | Val | Arg | |
| | | | 20 | | | | | 25 | | | | | 30 | | | |
| AAG | CAT | GTT | GCT | AAC | GGT | AAA | CGT | GTT | CGT | GAT | TTT | AAA | ATC | AGT | CCT | 144 |
| Lys | His | Val | Ala | Asn | Gly | Lys | Arg | Val | Arg | Asp | Phe | Lys | Ile | Ser | Pro | |
| | | 35 | | | | | 40 | | | | | 45 | | | | |
| ACT | TTT | ATC | CTT | GGC | GCA | GGT | CAT | GTT | ACA | TTC | TTT | TAC | GAT | AAG | CTC | 192 |
| Thr | Phe | Ile | Leu | Gly | Ala | Gly | His | Val | Thr | Phe | Phe | Tyr | Asp | Lys | Leu | |
| | | 50 | | | | | 55 | | | | | 60 | | | | |
| GAG | TTC | TTA | CGT | AAA | CGT | CAA | ATT | GAG | CTT | ATA | GCT | GAA | TGT | TTA | AAA | 240 |
| Glu | Phe | Leu | Arg | Lys | Arg | Gln | Ile | Glu | Leu | Ile | Ala | Glu | Cys | Leu | Lys | |
| 65 | | | | | 70 | | | | | 75 | | | | | 80 | |
| CGT | GGT | TTT | AAT | ATC | AAG | GAT | ACT | ACA | GTC | CAG | GAT | ATT | AGT | GAT | ATT | 288 |
| Arg | Gly | Phe | Asn | Ile | Lys | Asp | Thr | Thr | Val | Gln | Asp | Ile | Ser | Asp | Ile | |
| | | | | 85 | | | | | 90 | | | | | 95 | | |
| CCT | CAG | GAA | TTC | CGT | GGT | GAT | TAT | ATT | CCC | CAT | GAA | GCT | TCT | ATT | GCT | 336 |
| Pro | Gln | Glu | Phe | Arg | Gly | Asp | Tyr | Ile | Pro | His | Glu | Ala | Ser | Ile | Ala | |
| | | | 100 | | | | | 105 | | | | | 110 | | | |
| ATA | TCA | CAA | GCT | CGT | TTA | GAT | GAA | AAA | ATT | GCA | CAA | CGT | CCT | ACT | TGG | 384 |
| Ile | Ser | Gln | Ala | Arg | Leu | Asp | Glu | Lys | Ile | Ala | Gln | Arg | Pro | Thr | Trp | |
| | | 115 | | | | | 120 | | | | | 125 | | | | |
| TGG | AAA | TAC | TAC | GGT | AAG | GCG | ATT | TAT | GCA | TAA | | | | | | 417 |
| Trp | Lys | Tyr | Tyr | Gly | Lys | Ala | Ile | Tyr | Ala | | | | | | | |
| 130 | | | | | 135 | | | | | | | | | | | |

(2) INFORMATION FOR SEQ ID NO:4:

(i) SEQUENCE CHARACTERISTICS:
    (A) LENGTH: 138 amino acids
    (B) TYPE: amino acid
    (D) TOPOLOGY: linear (ii) MOLECULE TYPE: protein (x i) SEQUENCE DESCRIPTION: SEQ ID NO:4:

| | | | | | | | | | | | | | | |
|---|---|---|---|---|---|---|---|---|---|---|---|---|---|---|
| Met | Thr | Arg | Ile | Asn | Leu | Thr | Leu | Val | Ser | Glu | Leu | Ala | Asp | Gln | His |
| 1 | | | | 5 | | | | | 10 | | | | | 15 | |
| Leu | Met | Ala | Glu | Tyr | Arg | Glu | Leu | Pro | Arg | Val | Phe | Gly | Ala | Val | Arg |
| | | | 20 | | | | | 25 | | | | | 30 | | |
| Lys | His | Val | Ala | Asn | Gly | Lys | Arg | Val | Arg | Asp | Phe | Lys | Ile | Ser | Pro |
| | | 35 | | | | | 40 | | | | | 45 | | | |
| Thr | Phe | Ile | Leu | Gly | Ala | Gly | His | Val | Thr | Phe | Phe | Tyr | Asp | Lys | Leu |
| | | 50 | | | | | 55 | | | | | 60 | | | |
| Glu | Phe | Leu | Arg | Lys | Arg | Gln | Ile | Glu | Leu | Ile | Ala | Glu | Cys | Leu | Lys |
| 65 | | | | | 70 | | | | | 75 | | | | | 80 |
| Arg | Gly | Phe | Asn | Ile | Lys | Asp | Thr | Thr | Val | Gln | Asp | Ile | Ser | Asp | Ile |
| | | | | 85 | | | | | 90 | | | | | 95 | |
| Pro | Gln | Glu | Phe | Arg | Gly | Asp | Tyr | Ile | Pro | His | Glu | Ala | Ser | Ile | Ala |
| | | | 100 | | | | | 105 | | | | | 110 | | |
| Ile | Ser | Gln | Ala | Arg | Leu | Asp | Glu | Lys | Ile | Ala | Gln | Arg | Pro | Thr | Trp |
| | | 115 | | | | | 120 | | | | | 125 | | | |
| Trp | Lys | Tyr | Tyr | Gly | Lys | Ala | Ile | Tyr | Ala | | | | | | |
| 130 | | | | | 135 | | | | | | | | | | |

T4 ENDONUCLEASE V DNA REPAIR ENZYME HAVING SPECIFIC ACTIVITY AT LOW SALT CONCENTRATIONS

This invention was made with Government support under ES0409 awarded by the National Institutes of Health. The Government has certain rights in the invention.

This application is a continuation-in-part of application Ser. No. 401,916, filed Sept. 1, 1989, now abandoned.

TECHNICAL FIELD

The present invention relates to a DNA repair enzyme, T4 endonuclease V, having a complete specificity for DNA containing either pyrimidine dimers or apurinic/apyrimidinic sites. More specifically, the present invention relates to alterations in the pyrimidine dimer binding domain of the enzyme for increasing its specific activity at low salt concentrations.

BACKGROUND OF THE INVENTION

The small size of endonuclease V from bacteriophage T4, combined with the relative complexity of the reactions it catalyzes, makes it an interesting and important DNA repair enzyme to be structurally characterized. Among the T-even bacteriophages, T4 has been shown to be approximately twice as resistant to ultraviolet light inactivation as T2 and T6. Luria, S. E. (1947) Reactivation of a Radiated Bacteriophage by Transfer of Self-reproducing Units, Proc. Natl. Acad. Sci. 33, 253–264. Endonuclease V is coded for by the den V gene. Endonuclease V has been shown by biochemical and genetic analysis to possess four distinctly separable activities: (1) a pyrimidine dimer-specific DNA binding activity; (2) a pyrimidine dimer N-glycosylase activity; (3) an apyrimidinic/apurinic (AP)-endonuclease activity which may be manifest at the site of the N-glycosylase event or which may incise DNA at the site of any missing base; and (4) a salt sensitive linear diffusion along double-stranded DNA.

Site-directed mutational studies of the carboxyl terminal region of the enzyme support the concept that this part of the enzyme is intimately involved in binding to DNA at the site of the pyrimidine dimer. This carboxy terminal region of endonuclease V is essential for pyrimidine dimer binding.

The endonuclease V enzyme has commercial potential for in vivo as well as in vitro studies and uses. Especially for in vitro studies, it is desirable to possess an altered endonuclease V enzyme having increased specific activity thereby requiring less enzyme to provide a predetermined specific activity.

The present invention provides a T4 endonuclease V repair enzyme having increased specific activity at low salt concentrations.

SUMMARY OF THE INVENTION

A T4 endonuclease V DNA repair enzyme contains an amino acid sequence found within the carboxyl terminal portion of the enzyme which is required for pyrimidine dimer specific DNA binding. The region includes polar, nonaromatic amino acids and aromatic amino acids between amino acid 128 to 137 positions. The terminal region of the enzyme includes additional less polar aromatic moieties for increasing the specific activity of the enzyme at low salt concentrations.

The invention further provides a method of increasing the specific activity of T4 endonuclease V DNA repair enzyme, the method including the steps of increasing the aromatic composition of the enzyme at the carboxyl terminal region and performing specific nicking assays at low salt concentration.

FIGURES IN THE DRAWINGS

Other advantages of the present invention will be readily appreciated as the same becomes better understood by reference to the following detailed description when considered in connection with the accompanying drawings wherein:

FIG. 1 (A & B) shows colony forming ability of UV-irradiated E.coli cells harboring various denV gene constructs. Cells were grown for 16 hours at 30° C. in Luria broth (LB) containing 100 μg/ml ampicillin (amp). Appropriate dilutions of cells were plated and UV-irradiated on LB-amp plates and incubated at 30° C. for 36 hours.

Symbols for Panels A and B:

Panel A

○—AB2480 with pGX2608-16 (wild type denV)
●—AB2480 with pGX2608 (starting plasmid with no denV gene)
△—AB2480 with pGX2608-16 Tyr129→Phe
□—AB2480 with pGX2608-16 Tyr129→Trp Panel B ○—AB2480 with pGX2608-16 (wild type denV)
●—AB2480 with pGX2608 (starting plasmid with no denV gene)
—AB2480 with pGX2608-16 Tyr129→Stop
—AB2480 with pGX2608-16 Tyr129→Ser
—AB2480 with pGX2608-16 Tyr129→Frameshift
+—AB2480 with pGX2608-16 Tyr129—3 bp Deletion;

FIG. 2 (A,B,C) shows pyrimidine dimer-specific nicking activity of T4 endonuclease V mutants under processive nicking conditions. $^3$H-pBR322 DNA containing 25 pyrimidine dimers per molecule in 10 mM Tris (pH 8.0), 1 mM EDTA, 10 mM KCl, 10% (v/v) ethylene glycol were reacted with various amounts of wild type and mutant endonuclease V for 60 minutes at 37° C. After terminating the reactions with 1% SDS, DNAs were separated by agarose gel electrophoresis and the amount of DNA in forms I, II and III was determined;

Symbols for Panels A, B, C:
○—wild type T4 endonuclease V
△—mutant endonuclease V Tyr129→Phe
□—mutant endonuclease V Tyr129→Trp
  Panel A: Percentage of form I DNA remaining
  Panel B: First-order rate of loss in mass fraction of form I DNA
  Panel C: Percentage of Form III DNA
  Panel D: The intracellular accumulation of the following endonuclease V mutants was below the level which could be quantitated accurately by Western blot analysis. Thus sonicated extracts of known concentrations of soluble proteins were tested for pyrimidine dimer-specific nicking activity.
●—AB2480 with pGX2608
—AB2480 with pGX2608-16 Tyr129→Stop
—AB2480 with pGX2608-16 Tyr129→Ser
—AB2480 with pGX2608-16 with Tyr129→Frameshift
+—AB2480 with pGX2608-16 Tyr129→3 bp Deletion;

FIG. 3 (A & B) shows pyrimidine dimer-specific nicking of T4 endonuclease V mutants under distributive nicking assay conditions. $^3$H-pBR322 DNA containing 25 pyrimidine dimers per molecule in 10 mM Tris-HCl (pH 8.0), 1 mM EDTA, 100 mM KCl, 10% (v/v) ethylene glycol was reacted with 1.25 ng of wild type and mutant endonuclease V for various times at 37° C. After terminating the reactions by the addition of SDS to 1%, the DNAs were separated by agarose gel electrophoresis and the amount of DNAs in forms I and II was determined.

Symbols for Panels A and B:
○—wild type T4 endonuclease V
△—endonuclease V Tyr129→Phe
☐—endonuclease V Tyr129→Trp Panel A: Percentage of form I DNA remaining throughout the time-course nicking reaction.

Panel B: First-order rate of loss in the mass fraction of form I DNA; and

FIG. 4 (A & B) shows inhibition of complete incision activity of pyrimidine dimers by methoxyamine.

Symbols for Panels A and B:
○—1.25 ng wild type endonuclease V
△—0.5 ng endonuclease V Tyr129→Phe
☐—1.25 ng endonuclease V Tyr129→Trp Panel A: $^3$H-pBR322 DNA containing 25 pyrimidine dimers per molecule in 10 mM Tris-HCl (pH 8.0), 1 mM EDTA, 100 mM KCl, 10% (v/v) ethylene glycol and +various concentrations of methoxyamine (addition form a 1M methoxyamine-HCl, pH 7.5 stock) were reacted with wild type and mutant endonuclease V for 1 hour at 37° C. After terminating the reactions with the addition of 1% SDS, the DNAs were separated by agarose gel electrophoresis and quantitated.

Panel B: Reaction velocity k in the presence of various concentrations of methoxyamine were $$k = \frac{-\ln \frac{\text{form } I \text{ at [methoxyamine]}}{\text{form } I \text{ initial}}}{(\text{time}) (ng \text{ endonuclease } V)}$$

DETAILED DESCRIPTION OF THE INVENTION

In accordance with the present invention, a T4 endonuclease V DNA repair enzyme includes an amino acid sequence including a carboxyl terminal region for pyrimidine dimer binding of a specific activity. The sequence of the T4 endonuclease V gene (denV) and coded for amino acids is given in Table 4 (Valerie, K. et al Identification, physical map location, and sequence of the denV gene from bacteriophage T4. *Nucleic Acid Res.* 12:8085–8096 (1984)). The carboxyl terminal region of the endonuclease V enzymes spans Trp-128 to Tyr-137 (Trp-Tyr-Lys-Tyr-Tyr-Gly-Lys-Ala-Ile-Tyr). The C terminal region of endonuclease V enzyme is capable of binding the kinked, partially single stranded DNA at the site of a pyrimidine dimer.

The present invention is based on studies showing the terminal region including substitutions of other less polar aromatic amino acids increases the specific activity of the enzyme at low salt concentrations. More specifically, in accordance with the present invention, aromatic amino acid substitutions (Phe 129, Trp 129) for a more polar aromatic amino acid (Tyr 129) at the terminal region increases the specific activity of the endonuclease enzyme.

In accordance with the following experimental evidence, mutant enzymes including substitutions Tyr-129→Phe (Sequence ID Nos. 1 and 2) and Tyr-129→Trp (Sequence ID Nos. 3 and 4) displayed a 1000% and 500% enhanced specific nicking activity respectively. These reactions were also shown to be completely processive. Assays performed at higher (100 mM) salt concentrations reduced the specific activities of the mutant enzymes approximately to that of the wild type enzyme for the Tyr-129→Phe mutant and 20% of that of the wild type for Tyr-129→Trp mutant as opposed to the activity of the mutant enzymes at lower salt concentrations below 25 mM. The specific activity of the mutant enzyme decreased approximately ten fold when assayed at physiological salt concentrations.

The following experimental evidence demonstrates the unexpected increase of activity of the enzyme used in accordance with the present invention.

A. EXPERIMENTATION

1. Materials and Methods

Bacteria, Phage and Plasmids

The *E.coli* strains, M13 phage constructs, T4 phage and plasmids which were utilized in this study are described in Table I.

Oligonucleotide Site-directed Mutagenesis

The construction of mutant den V genes was performed in M13 O$_L$P$_R$ den V by standard procedures. All oligonucleotides were synthesized on a Biosearch Cyclone ™ and purified as previously described. All mutants were verified by dideoxy sequencing methods. The den V structural gene was subcloned into pGX2608 as described in Recinos, A., III, Augustine, M. L., Higgins, K. M., Lloyd, R. S. "Expression of the bacteriophage T4 denV structural gene in *Escherichia coli*" J. Bacteriol. 168:1014–1018, 1986; Recinos, A. III, Lloyd, R. S. "Site-directed mutagenesis of the T4 endonuclease V gene: role of lysine-130."Biochemistry 27:1832–1838, 1988.

UV Survival of Bacteria and Complementation of T4 den V1 Phage

The procedures to asses UV survival of bacterial cultures and the complementation of UV-irradiated T4 denV1 phage as described in Recinos, A. III, Augustine, M. L. et al supra; Recinos, A. III, Lloyd, R. S. supra.

Purification of Mutant T4 Endonuclease V

Following the site-directed mutagenesis, sequencing and subcloning of the mutant den V genes into pGX2608, the mutant endonuclease V proteins were expressed off of the O$_L$P$_R$ hybrid promoter in *E. coli* AB2480 grown in 30° C. for 16 hours. Cells (100 ml) were pelleted by centrifugation at 4,500×g and resuspended in 10 ml cold 10 mM Tris-HCl (pH8.0), 1 mM EDTA, 100 mM KCl, 10% (v/v) ethylene glycol (Buffer A). Cells were disrupted by sonication and the cell debris removed by centrifugation at 10,000×g. The endonuclease V was batch absorbed for 16 hours at 4° C. onto 3 ml of single-stranded DNA agarose matrix. The single-stranded DNA agarose was pelleted by centrifugation at 1,000×g and the supernatant removed. The agarose matrix was washed 3 times, 10 ml each with Buffer A in order to remove any nonspecific proteins. The endonuclease V was eluted from the washed pellet by resuspending the pellet in buffer A containing 1M KCl. The amount of endonuclease V which was recovered by this procedure was determined by quantitative Western blot analyses in which pure endonuclease V was used to generate a standard curve.

Pyrimidine Dimer-specific Plasmid DNA Nicking Assay

The ability of the wild type and mutant endonuclease V molecules to produce single-strand breaks in UV-irradiated supercoiled covalently closed circular plasmid DNA (form I) was performed as follows.

$^3$H-pBR322 (1 µg/assay point) was UV-irradiated to produce approximately 25 pyrimidine dimers per DNA molecule. This DNA, in either 10 mM Tris-HCl (pH8.0), 1 mM EDTA, 10 mM KCl, 10% (v/v) ethylene glycol or the same as above except 100 mM KCl, was incubated either with varying concentrations of endonuclease V or with a known concentration of enzyme for increasing amounts of time. Reactions were terminated by the addition of an equal volume of 50 mM Tris-HCl (pH8.0) 10 mM EDTA, 2% SDS, 20% (w/v) sucrose and 0.025% (w/v) bromphenol blue.

Nicking assays which measured the inhibition of only the phosphodiester bond scission were performed in either 20 mM Tris-HCl (pH 8.0), 1 mM EDTA, 100 mM KCl, 10% (v/V) ethylene glycol and various concentrations of methoxyamine. Reactions were terminated as described above. The plasmid DNA reaction products were separated by agarose gel electrophoresis and after the DNAs were visualized by ethidium bromide staining, the individual bands were excised from the gel and quantitated as previously described.

RESULTS

UV Survival of DNA Repair-deficient Cells Harboring Mutant denV Genes

Figure 1A:
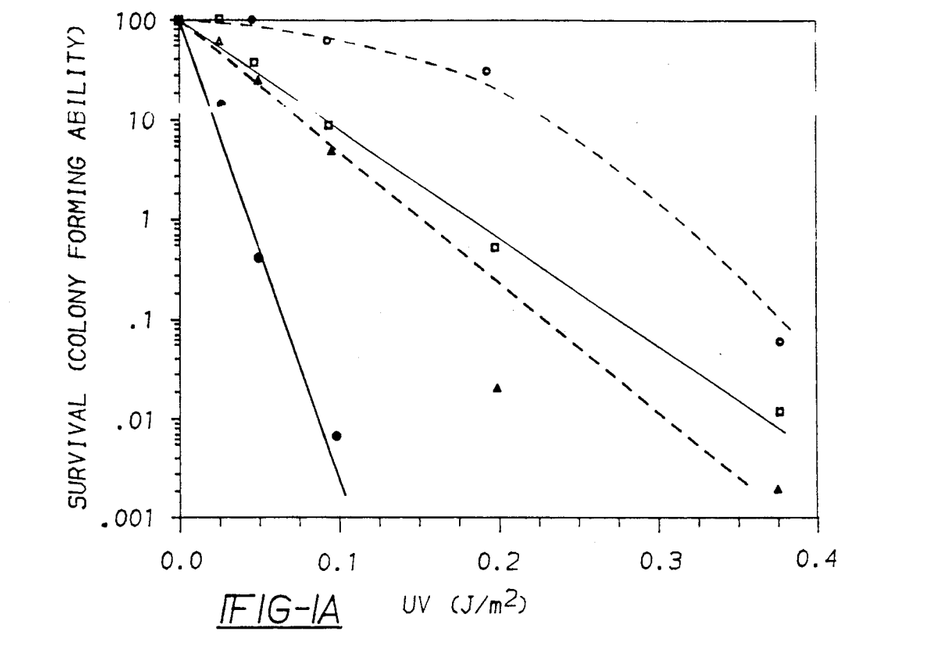
Figure 1B:
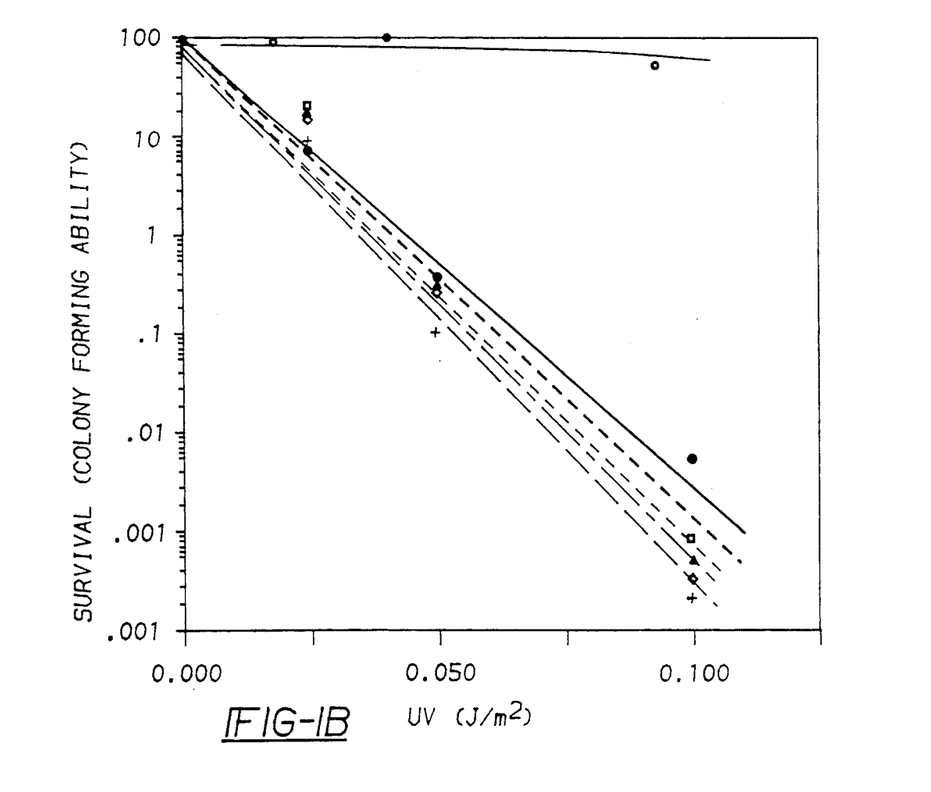

The technique of oligonucleotide site-directed mutagenesis was used to create a series of mutations within the T4 denV gene which had been previously subcloned into M13mp18. The mutated genes, which are categorized in Table I, were identified and purified by differential hybridization and verified by dideoxy sequencing techniques. The altered denV structural genes were then excised by ClaI digestion from M13 RF and subcloned into pGX2608, an expression vector which contains a unique ClaI site downstream of hybrid 2 promoter $O_LP_R$. Plasmids were transformed into E.coli AB2480 (uvrA-recA-) and the correct orientation of the denV gene relative to the promoter was verified by restriction enzyme analyses. Individual colonies were grown at 30° C. and tested as to whether the mutant endonuclease V enzymes were capable of conferring enhanced UV resistance to excision-and recombination-deficient E.coli (FIG. 1). As previously demonstrated, the expression of wild type endonuclease V (open circles) in these cells results in a significant enhancement in UV survival relative to that of cells which only harbor the parental vector PGX2608 (Closed circles). FIG. 1, Panel A shows that the substitutions of Tyr129→Trp (□) and Tyr 129→Phe (Δ) in accordance with the present invention produce enzymes whose phenotypic expression only results in approximately one-half the survival enhancement as compared to wild type. UV survival data for all other changes at the Tyr129 position (Ser, stop codon, deletion and frameshift) resulted in UV survivals which were indistinguishable from denV gene being absent from these cells (FIG. 1, Panel B). These data, coupled with previous findings suggest that there is a strong requirement for an aromatic amino acid at this position within the enzyme and these in vivo analyses would suggest that the native tyrosine at position 129 is best suited for conferring resistance to the killing effects of UV.

Complementation of the T4 denV1 Phage

The cytosine bases within the genome of bacteriophage T4 DNA are modified to glucosylated-5-hydroxymethyl cytosine. It is probably this modification of its DNA which renders the normal E.coli DNA repair enzyme systems unable to initiate repair on damaged UV-irradiated T4 DNA. However, if UV-irradiated T4 denV1 phage infect E.coli cell which contains functional endonuclease V, survival is enhanced. Therefore E.coli harboring each of the mutant T4 endonuclease V constructions were infected with the T4 denV1 phage which had previously been exposed to various UV dosages. The data summarizing UV dosages required to reduce the phage survival to 10% ($D_{10}$) are presented in Table II. These data demonstrate that the only two mutants which were capable of enhancing phage survival were the Tyr129→Trp and Tyr129→Phe of the present invention. These data are in good agreement with the UV survival as measured by colony forming ability. The degree of enhanced phage survival closely parallel that observed for cell survival.

Pyrimidine Dimer-specific Nicking Activity Assays

The wild type endonuclease V locates dimers within DNA through a one-dimensional diffusion mechanism along DNA both in vivo and in vitro at monovalent salt concentrations below 40 mM. In vitro location of dimers and subsequent incision reactions above 40 mM salt proceed by way of a 3-dimensional search through the reaction medium. In order to evaluate the dimer-specific nicking activity of the mutant enzymes of the present invention relative to wild type, E. coli AB2480 harboring various mutant denV expression plasmids were grown and the enzymes were partially purified (to approximately a 10% purity). Whenever possible, the amount of enzyme was determined by quantitative Western blot analyses as previously described. Two of the mutant proteins, Tyr129→Trp and Tyr129→Phe accumulated to levels approximately 100% and 20%, respectively of those found for wild type enzyme (data not shown).

Although both sets of in vivo data, presented in FIG. 1 and Table II, suggested that the Tyr129→Trp and Tyr129→Phe would have much lower specific activities relative to wild type, a pyrimidine dimer-specific nicking assay, carried out under processive enzyme conditions (low salt) suggested that both of these mutants had enhanced specific activities (FIG. 2, Panels A and B). When the rapid loss of UV-irradiated form I DNAs (Panel A) for Tyr129→Phe (Δ) and Tyr129→Trp (□) and wild type (○) are converted into a relative first-order rate constant (Panel B) the Tyr129→Phe and Tyr129→Trp show a 10- and 5-fold enhanced specific activity respectively over that of wild type.

Figure 2A:
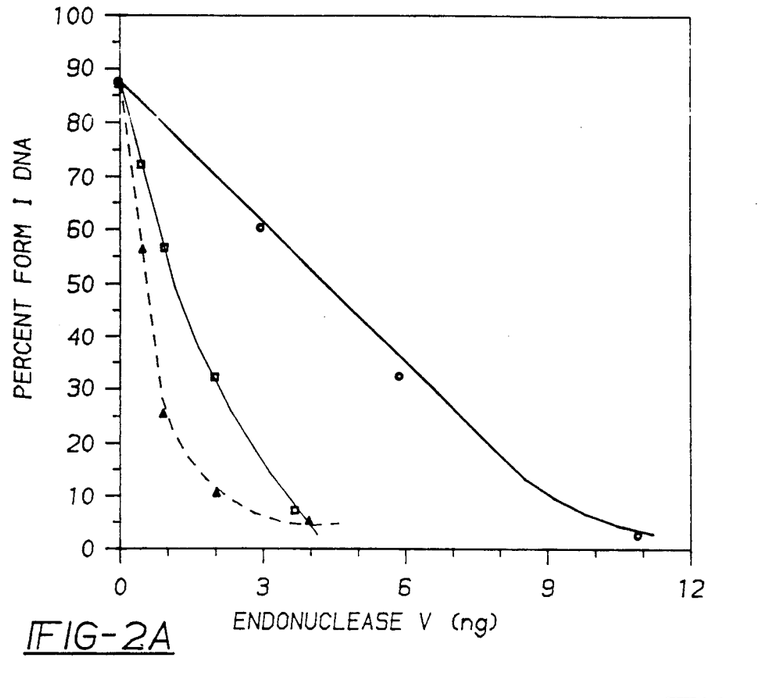
Figure 2B:
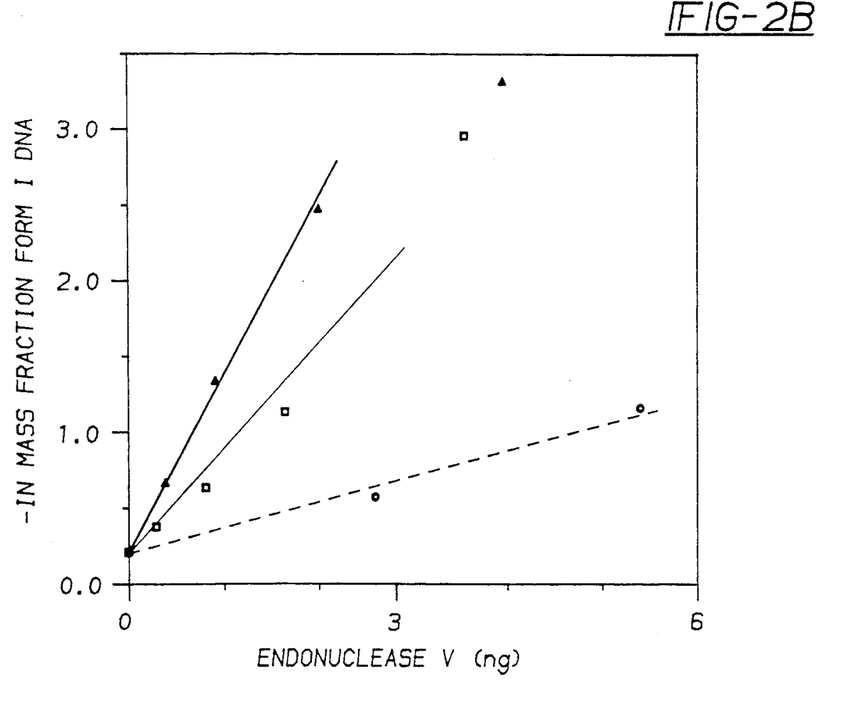
Figure 2C:
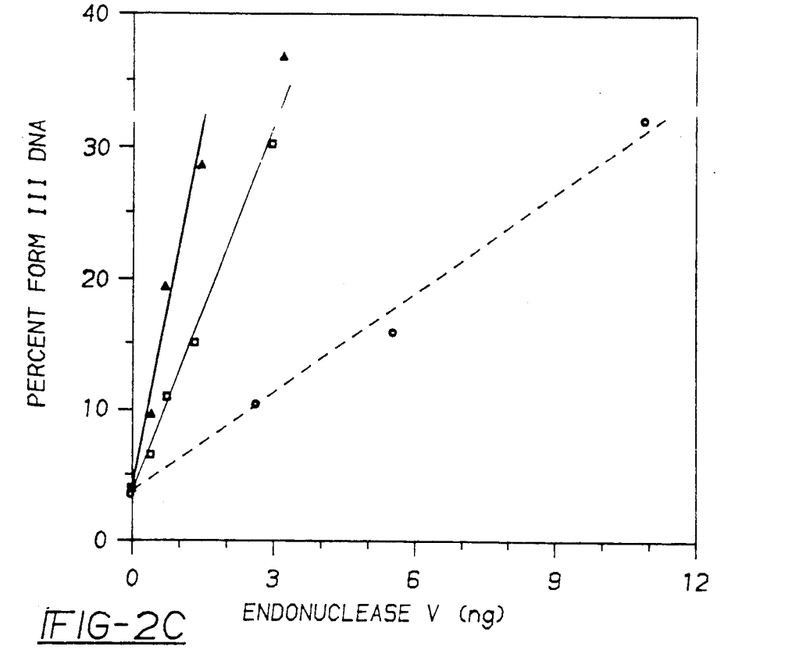

In addition to monitoring the loss of form I DNA, a processive nicking reaction is always characterized by a linear increase in the percentage of form III DNA (full-length linear DNA) as the reaction proceeds. Form III DNA is generated when endonuclease V incises pyrimidine dimers in close proximity and on complementary strands. This is a direct consequence of processive sliding and nicking. The percentage of accumulated form III DNA was measured in the experiment described above (Panel C). The accumulation of form III DNA was linear and significantly more rapid for the two mutants relative to wild type. This correlates well with the enhanced rate of loss of form I DNA in these mutants. Table III relates the percentage of form I DNA remaining with the present form III DNA accumulated. For all data points and for all mutants, a given reduction in form I DNA always generated the same percentage of form III DNA, thus providing that both the Tyr129→Phe and Tyr129→Trp mutants like the wild type, act processively in vitro at low salt concentrations.

Thus if mutant endonuclease V molecules are functioning *in vivo* by a similar processive scanning mechanism to that of the wild type enzyme, these results could suggest that enhanced specific activities do not necessarily correlate with enhanced UV survival. In that scenario, the extremely rapid production of single-strand breaks (and possibly double-strand breaks) by the mutant enzymes may occur too rapidly for the successive steps in the DNA repair mechanism, thus leading to cellular death. The repair of UV-irradiated plasmid DNA occurs in two phases: the rapid processive nicking reaction which was catalyzed by endonuclease V and a slower processive mechanism including repair patch synthesis, ligation and supercoiling.

Figure 2D:
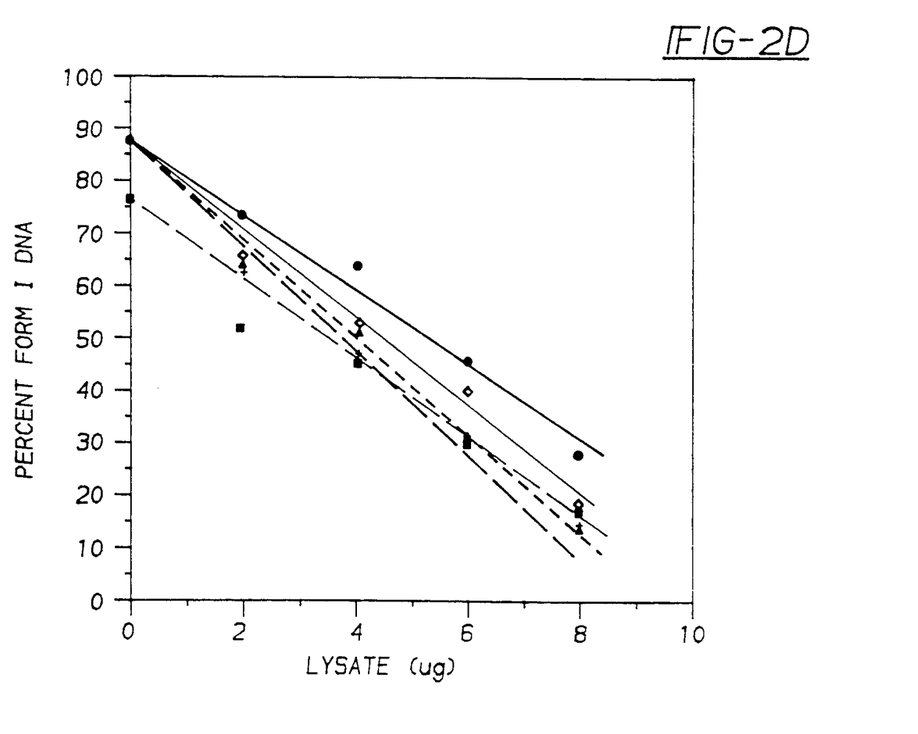

The levels of intracellular accumulation of the remainder of the denV mutants was below the level of detection by Western blot analyses (data not shown). Therefore nicking assays were performed using sonicated cell extracts in which the same total amount of cellular protein were added to the dimer nicking assay (Panel D). Since there was very little activity in these mutant cell extracts relative to AB2480-pGX2608 cell extracts (○) and since precise enzyme quantitation was not possible, no further analyses were carried out on these mutants.

Figure 3A:
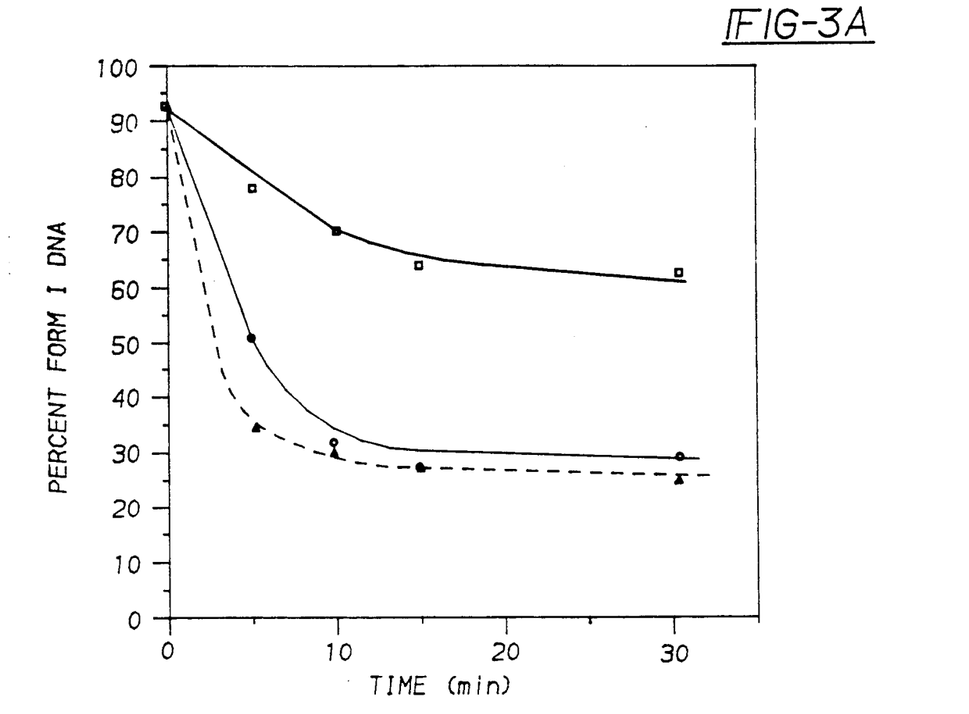
Figure 3B:
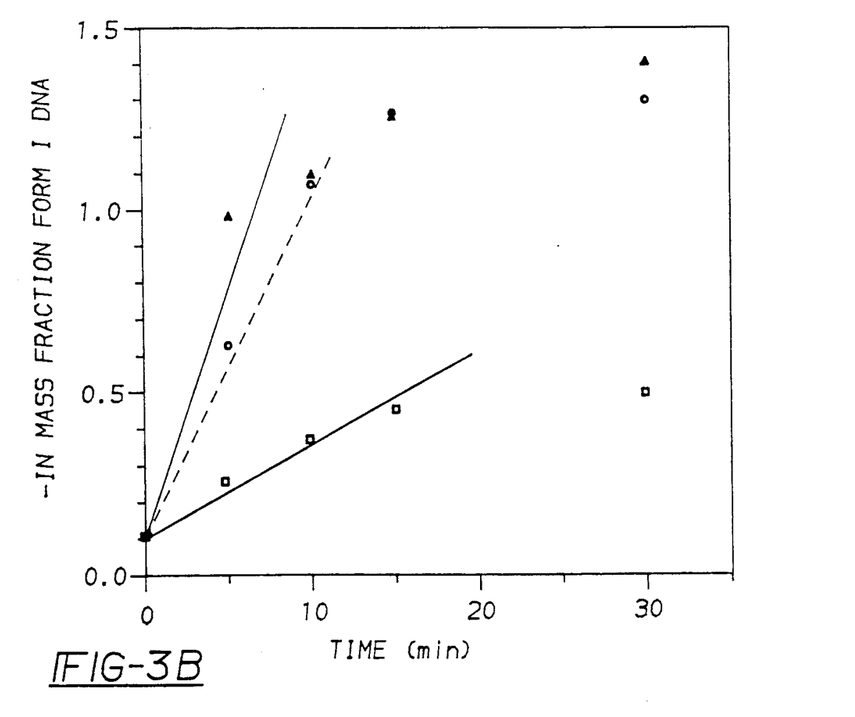

In addition to monitoring the specific activity of the mutant enzymes under processive nicking conditions, experiments were also carried out with a distributive nicking assay in which dimers are located through a 3-dimensional search. A total of 1.25 ng each of wild type (○), Tyr129→Phe (Δ) and Tyr129→Trp (□) were incubated with UV-irradiated DNA for increasing amounts of time (FIG. 3). In contrast to the results observed under processive nicking conditions, the wild type and Tyr129→Phe appear to have an identical specific activity while Tyr129→Trp was reduced to 20% that of wild type. No form III DNA was produced, in any of these reactions, thus suggesting that at 100 mM salt, all of the enzymes tested were functioning in a distributive manner. These results may suggest that the *in vitro* data generated under the processive, low-salt conditions reflect a subtle alteration in the 3-dimensional structure of the enzyme at low salt in order to achieve the enhanced specific activities.

Inhibition of Phosphodiester Bond Scission at Pyrimidine Dimers with Methoxyamine The rate-limiting step in endonuclease V's formation of the complete incision in the phosphodiester backbone at the site of a dimer has been proposed to be the phosphodiester bond scission rather than binding or glycosylic bond scission (reviewed by Friedberg, Dodson and Lloyd, McMillan et al, and Liuzzi et al). It has been postulated that the endonuclease must dissociate from the dimer site after making the glycosylic bond scission and reassociate, presumably in a different conformation to catalyze the phosphodiester bond scission. Such a model explains the accumulation of DNA with a high frequency of glycosylic bond scissions and few compete incisions when the reactions are performed at elevated pH.

Figure 4A:
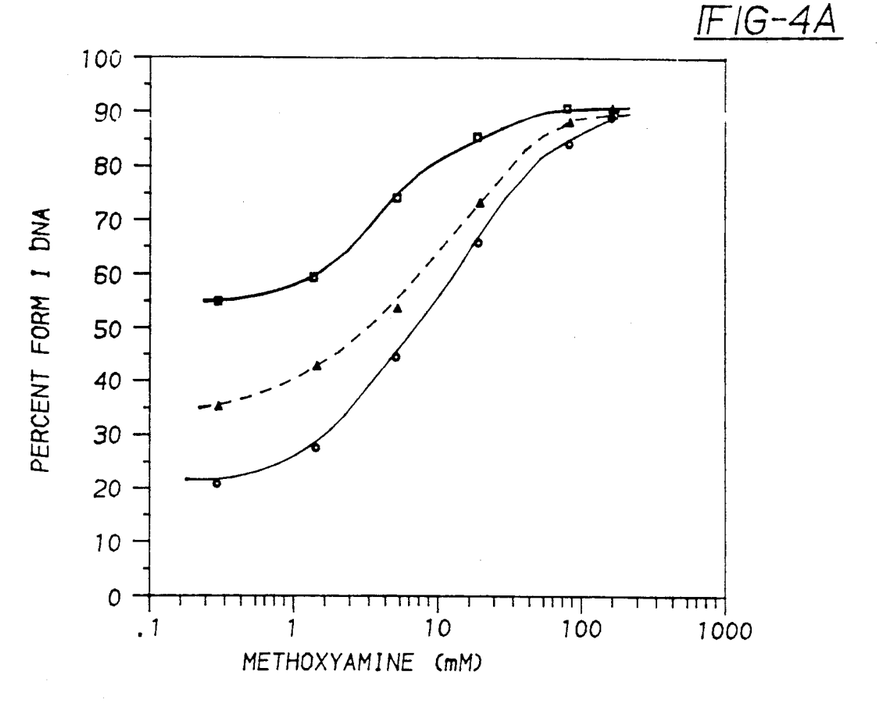
Figure 4B:
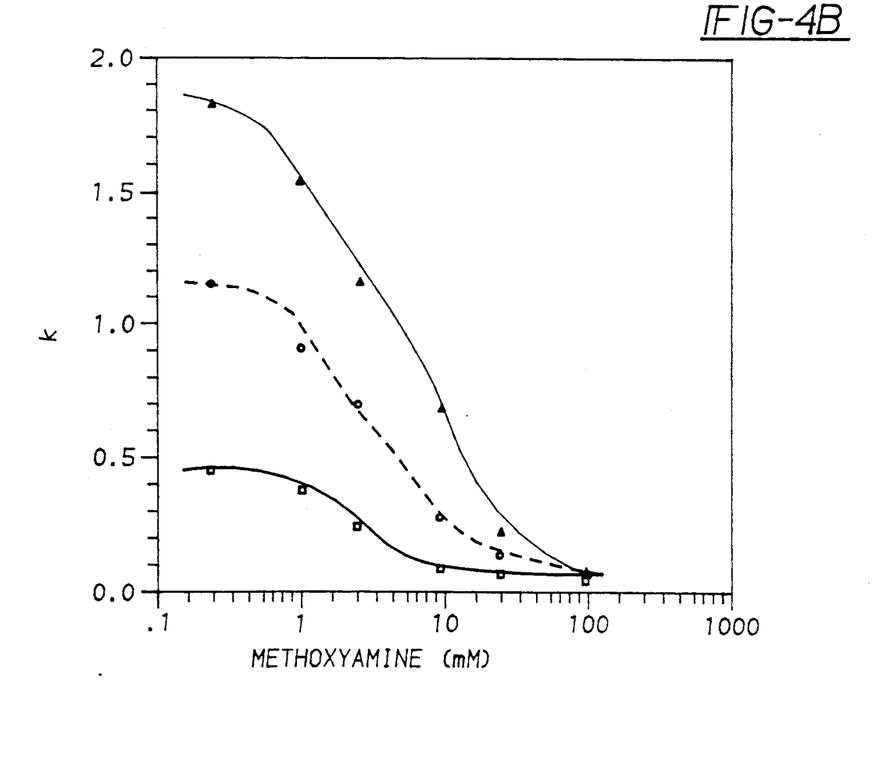

In order to completely uncouple the glycosylase activity from the subsequent phosphodiester bond cleavage, Liuzzi et al demonstrated that the addition of 50 mM methoxyamine to the reaction mixture completely inhibited the phosphodiester bond scission activity but had no effect on the rate of glycosylase activity. Therefore in order to test whether the observed enhanced specific activities are due to a significant increase in the rate of phosphodiester bond scission, the effect of increasing methoxyamine concentrations in the reaction mixtures was measured. Experiments were performed in which the concentration of methoxyamine required to inhibit to 50% the phosphodiester bond scission activity was determined for the wild type and mutant enzymes (FIG. 4). Using limiting amounts of enzyme, the percent of form I DNA was followed as the concentration of methoxyamine was varied over nearly 3 orders of magnitude (FIG. 4, Panel A). The relative velocities of the reactions were calculated and are shown in FIG. 4, Panel B. The 50% methoxyamine-induced inhibition was achieved at 2.5 mM for both wild type and Tyr129→Trp mutant, while 4.0 mM was required for the Tyr129→Phe mutant. Thus, it appears that if the rate of phosphodiester bond scission is the enhanced activity in these mutants, then the rate of methoxyamine reaction on the sugar is orders of magnitude greater than that of the endonuclease V-catalyzed incision. In these experiments the enhanced specific activity measurements would be masked by the methoxyamine reaction.

The above experimental data and discussion shows that the enzymes of the present invention exhibit elevated specific activities when the enzymes are assayed under low salt concentrations. The specific activities of these enzymes decrease approximately 10-fold when assayed at physiological salt concentrations. The results of the in vivo assays which measured the biological impact of the production of the enzymes of the present invention in DNA repair-deficient *E. coli* are consistent with the hypothesis of the inventor that a too rapid production of single-strand breaks in the cellular DNA may least to cell killing. This temporal uncoupling of the incision step from the subsequent repair synthesis, ligation and supercoiling may be deleterious to survival. The enzymes of the present invention may undergo subtle structural alterations at lower salt concentrations which in turn reflect elevated specific activities.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

TABLE I

E. coli, Phage and Plasmids Used in this Study

| Strain, plasmid or phage | Genotype or phenotype | Source |
|---|---|---|
| *E. coli* | | |
| UT481 | met thy Δ(lac-pro) hsdRBamHI hsdM+ supD Tn10/F' traD36 proAB lacIqZΔM15 | C. Lark, U. Utah |
| AB2480 | uvrA6 recA13 | A. Ganesan, Stanford U. |
| Plasmid | | |
| pGX2608 | Ap$^r$λO$_L$P$_R$λt$_{4S}$GalK+ | Genex Corp. |
| pGX2608-16-denV+ | Ap$^r$λO$_L$P$_R$ endonuclease V+ λt$_{4S}$GalK+ | Recinos & Lloyd[20] |
| pGX2608-16-denV Tyr129 → Trp | New 129 Codon TGG | This study |
| pGX2608-16-denV Tyr129 → Phe | New 129 Codon TTT | This study |
| pGX2608-16-denV Tyr129 → Stop | New 129 Codon TAA | This study |
| pGX2608-16-denV Tyr129 → Ser | New 129 Codon TCT | This study |
| pGX2608-16-denV Tyr129 → Deletion | Codon Deleted at 129 | This study |
| pGX2608-16-denV Tyr129 → Frameshift | frameshift of 2 bp | This study |
| Phage | | |
| M13mp18-O$_L$P$_R$denV | | Recinos & Lloyd[22] |
| M13mp18-O$_L$P$_R$denV Tyr129 → Trp | | This study |
| M13mp18-O$_L$P$_R$denV Tyr129 → Phe | | This study |
| M13mp18-O$_L$P$_R$denV Tyr129 → Stop | | This study |
| M13mp18-O$_L$P$_R$denV Tyr129 → Ser | | This study |
| M13mp18-O$_L$P$_R$denV Tyr129 → Deletion | | This study |
| M13mp18-O$_L$P$_R$denV Tyr129 → Frameshift | | This study |
| wild type T4 | | A. Ganesan, Stanford U. |
| T4v1 denV | | A. Ganesan, Stanford U. |

TABLE II

Complementation of the Mutant T4 denV1 Phage

| E. coli AB2480 cells with plasmids* | Phage T4 WT | Phage T4 denV1 | D$_{10}$ (J/m$^2$) | Survival enhancement | Percent of maximal survival enhancement** |
|---|---|---|---|---|---|
| pGX2608 | + | | 5 | 1.67 | 100 |
| pGX2608 | | + | 3 | 1.00 | 0 |
| pGX2608-16(WT endonuclease V) | + | | 5 | 1.67 | 100 |
| pGX2608-16(WT endonuclease V) | | + | 4.6 | 1.53 | 79 |
| pGX2608 Tyr129 → Trp | | + | 4.5 | 1.50 | 75 |
| pGX2608 Tyr129 → Phe | | + | 3.8 | 1.27 | 40 |
| pGX2608 Tyr129 → Stop | | + | 3.0 | 1.00 | 0 |
| pGX2608 Tyr129 → Ser | | + | 3.0 | 1.00 | 0 |
| pGX2608 Tyr129 → Deletion | | + | 3.0 | 1.00 | 0 |

*Stationary phase *E. coli* cells were diluted 1:100 into LB-amp media and grown at 30° C. until cells were in mid-log phase (approximately 5 × 10$^8$ cells/ml). Various dilutions of irradiated and unirradiated T4 wild type phage and T4 denV1 were mixed with 2.5 × 10$^8$ cells and plated in 5 ml of 0.7% agarose in LB-amp on 25-ml 1.5% agar LB-amp plates. Phage were grown at 30° for 24 hours.
The UV dose given to the T4 phage which resulted in a 10% plaque-forming ability.
Survival enhancement D$_{10}$/D$_{10}$ of T4 denV1 plated on AB2480 pGX2608.
**Percent of maximum survival enhancement = (D$_{10}$/D$_{10}$ of wild type T4 phage)(100%).

TABLE III

Correlation of the Loss of Form I DNA with Accumulation of Form III DNA-Evidence of Processivity

| | -ln form I ~0.56 | | -ln form I ~1.2 | | -ln form I ~3.2 | |
|---|---|---|---|---|---|---|
| | % form I | % form III | % form I | % form III | % form I | % form III |
| WT endonucleae V | 58.3 | 10.1 | 31.9 | 15.5 | 2.9 | 32.3 |
| endonuclease V Tyr129 → Trp | 55.3 | 10.6 | 33.1 | 15.7 | 5.5 | 29.8 |
| endonuclease V Tyr129 → Phe | 56.3 | 8.9 | 25.3 | 18.9 | 3.8 | 36.2 |

```
    Met Thr Arg Ile Asn Leu Thr Leu Val Ser Glu Leu Ala Asp Gln
TCGATG ACT CGT ATC AAC CTT ACT TTA GTA TCT GAA TTG GCT GAC CAA
|------|
Cla I

His Leu Met Ala Glu Tyr Arg Glu Leu Pro Arg Val Phe Gly Ala
CAC TTA ATG GCT GAA TAT CGT GAA TTG CCG CGT GTT TTT GGT GCA
```

-continued

```
Val  Arg  Lys  His  Val  Ala  Asn  Gly  Lys  Arg  Val  Arg  Asp  Phe  Lys
GTT  CGT  AAG  CAT  GTT  GCT  AAC  GGT  AAA  CGT  GTT  CGT  GAT  TTT  AAA

Ile  Ser  Pro  Thr  Phe  Ile  Leu  Gly  Ala  Gly  His  Val  Thr  Phe  Phe
ATC  AGT  CCT  ACT  TTT  ATC  CTT  GGC  GCA  GGT  CAT  GTT  ACA  TTC  TTT

Tyr  Asp  Lys  Leu  Glu  Phe  Leu  Arg  Lys  Arg  Gln  Ile  Glu  Leu  Ile
TAC  GAT  AAG  CTC  GAG  TTC  TTA  CGT  AAA  CGT  CAA  ATT  GAG  CTT  ATA
               XhoI/TaqI

Ala  Glu  Cys  Leu  Lys  Arg  Gly  Phe  Asn  Ile  Lys  Asp  Thr  Thr  Val
GCT  GAA  TGT  TTA  AAA  CGT  GGT  TTT  AAT  ATC  AAG  GAT  ACT  ACA  GTC

Gln  Asp  Ile  Ser  Asp  Ile  Pro  Gln  Glu  Phe  Arg  Gly  Asp  Tyr  Il
CAG  GAT  ATT  AGT  GAT  ATT  CCT  CAG  GAA  TTC  CGT  GGT  GAT  TAT  AT
                                        EcoRI

Pro  His  Glu  Ala  Ser  Ile  Ala  Ile  Ser  Gln  Ala  Arg  Leu  Asp  Gl
CCC  CAT  GAA  GCT  TCT  ATT  GCT  ATA  TCA  CAA  GCT  CGT  TTA  GAT  GA
              HindIII Lys  Ile  Ala  Gln  Arg  Pro  Thr  Trp  Tyr  Lys  Tyr  Tyr  Gly  Lys  Al
AAA  ATT  GCA  CAA  CGT  CCT  ACT  TGG  TAC  AAA  TAC  TAC  GGT  AAG  GC Ile  Tyr  Ala  ***                      ┌ClaI────┐
ATT  TAT  GCA  TAA  GGGAACAACCTGGACCTCATCGAT.
```

---

What is claimed is:

1. A T4 endonuclease V DNA repair enzyme comprising: an amino acid sequence including a carboxyl terminal region for pyrimidine dimer binding of a specific activity, said region including polar, nonaromatic amino acids and aromatic amino acids between amino acid 128 to 137 positions; characterized by said terminal region including an aromatic amino acid substitution different and less polar than tyrosine at position 129.

2. An enzyme as set forth in claim 1 further characterized by said aromatic amino acid substitution consisting of the substitution of phenylalanine for tyrosine at the 129 position of said enzyme *(Sequence I.D. No. 2)*.

3. An enzyme as set forth in claim 1 further characterized by said aromatic amino acid substitution consisting of the substitution of tryptophan for tyrosine at the 129 amino acid position of said enzyme *(Sequence I.D. No. 4)*.

4. A method of increasing the specific activity of T4 endonuclease V DNA repair enzyme having a carboxyl terminal region for pyrimidine dimer binding, said method including the steps of increasing the aromatic composition of the enzyme at the carboxy terminal by substituting an aromatic amino acid for a polar, nonaromatic amino acid at the 129 amino acid position terminal region.

5. A method as set forth in claim 4 wherein said substituting step is further defined as substituting phenylalanine for tyrosine at the 129 amino acid position of the enzyme *(Sequence I.D. No. 2)*.

6. A method as set forth in claim 4 wherein said substituting step is further defined as substituting tryptophan for tyrosine at the 129 amino acid position of the enzyme *(Sequence I.D. No. 4)*.

* * * * *